United States Patent [19]
Iizuka et al.

[11] Patent Number: 5,355,887
[45] Date of Patent: Oct. 18, 1994

[54] ULTRASONIC DIAGNOSTIC APPARATUS

[75] Inventors: Miyuki Iizuka; Akira Shiba; Isamu Yamada; Takaki Shimura, all of Kawasaki, Japan

[73] Assignee: Fujitsu Limited, Kawasaki, Japan

[21] Appl. No.: 968,688

[22] Filed: Oct. 30, 1992

[30] Foreign Application Priority Data

Oct. 31, 1991 [JP] Japan .................. 3-286207
Jul. 15, 1992 [JP] Japan .................. 4-187935

[51] Int. Cl.$^5$ ............................. A61B 8/00
[52] U.S. Cl. .................. 128/660.04; 128/660.07
[58] Field of Search ............. 128/660.01, 660.02, 128/660.07, 661.03, 661.04, 661.09

[56] References Cited

U.S. PATENT DOCUMENTS

| | | | |
|---|---|---|---|
| 4,660,564 | 4/1987 | Benthin et al. | 128/661.03 |
| 4,771,792 | 9/1988 | Seale | 128/774 |
| 5,086,775 | 2/1992 | Parker et al. | 128/660.01 |
| 5,178,147 | 1/1993 | Ophir et al. | 128/660.01 |

*Primary Examiner*—Francis Jaworski
*Attorney, Agent, or Firm*—Staas & Halsey

[57] ABSTRACT

The present invention relates to an ultrasonic echographic diagnostic apparatus which is capable of displaying the characteristics and properties of tissue, such as the maximum displacement of tissue, the hardness of tissue, the velocity of propagation of vibrations through tissue, and the magnitude and direction of movement of tissue, in various display modes. The apparatus is capable of detecting and displaying the displacement of tissue caused by heartbeat or external pressure in a real-time mode by calculating the minute displacement of tissue or the differential of the same, calculating a temporal local maximum of the minute displacement varying with time, time corresponding to the temporal local maximum, the gradient of the time and the absolute magnitude of the gradient, and displaying the results of the calculations. In another aspect of the invention, the apparatus specifies a desired point or points and a desired direction or directions in a tomogram, determines calculating data passing a desired point and extending along a desired direction, for a plurality of tomograms obtained at different times, respectively, by interpolating the data signals, determines the displacement of the desired point in the desired direction or the rate of change of the displacement on the basis of the calculating data, and displays the information calculated on the basis of the displacement or the rate of change of the displacement.

22 Claims, 14 Drawing Sheets

FRAME NO. 3     FRAME NO. 4     FRAME NO. 5

VECTOR REPRESENTATION

STREAMLINE
REPRESENTATION

VECTOR REPRESENTATION
OF GRADIENT POSTIVE
LOCAL MAXIMUM

VECTOR REPRESENTATION
OF GRADIENT TIME

TIME

DISPLACEMENT
(LOCAL MAXIMUM)

FRAME NO. 1   FRAME NO. 2   FRAME NO. 3

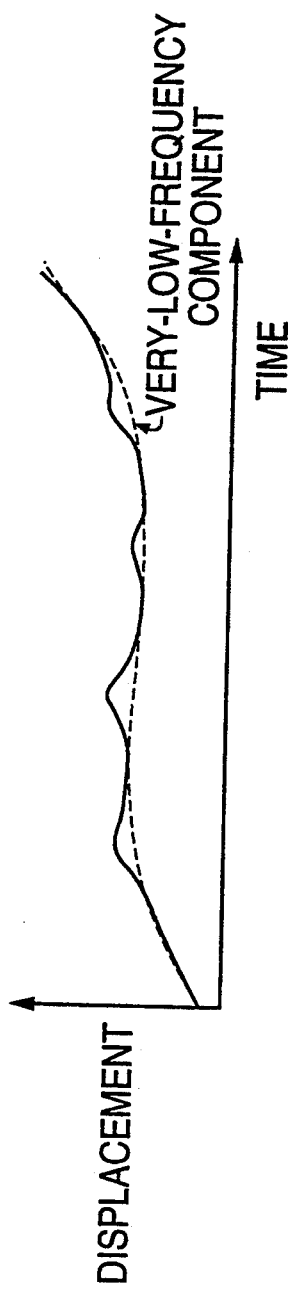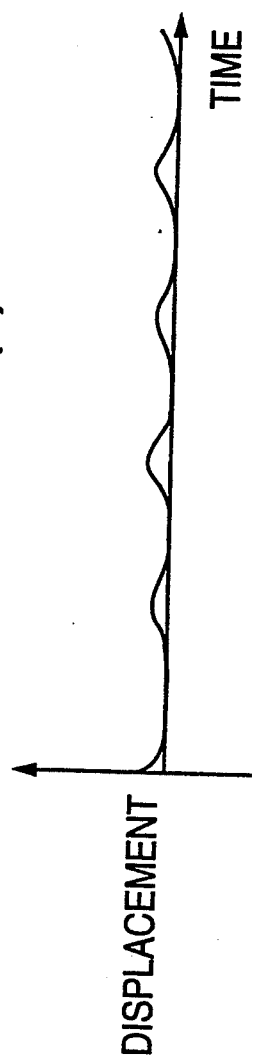

ULTRASONIC DIAGNOSTIC APPARATUS

BACKGROUND OF THE INVENTION

1. Field of the Invention

The present invention relates to an ultrasonic diagnostic apparatus which receives ultrasonic waves applied to, and reflected by a specimen to obtain signals representing the condition of the specimen, and produces a tomogram of a cross section of the specimen on the basis of the signals. More specifically, the present invention relates to an ultrasonic diagnostic apparatus featured by a display that displays a tomogram of a cross section of a specimen, and an ultrasonic diagnostic apparatus capable of calculating the displacement of vital tissues caused by pulsation or an external pressure, and of displaying the result of calculation.

2. Description of the Related Art

An ultrasonic diagnostic apparatus facilitates the diagnosis of diseased parts in a specimen, particularly in human body organs, by receiving ultrasonic waves applied to and reflected by the human body organs to obtain signals representing the condition of the human body organs. The ultrasonic diagnostic apparatus produces a picture of the human body organs on the basis of the signals, and the picture. Methods of determining small displacement of various parts of the human body in addition to producing tomograms have been proposed in, for example, Y. Araki, S. Yagi and K. Nakayama, "Local Displacement Velocity Analysis of Soft Tissue using Doppler Method", Proceedings of the 55th meeting on the Japan Society of Ultrasonics in Medicine, 55-314, PP. 689-690 (December 1989) (reference [1])

The method disclosed in the reference [1] applies a pulse ultrasonic beam to human body organs several times in the same direction and determines the minute displacement of parts at specific depths in the direction of travel of the pulse ultrasonic beam by the pulse Doppler method.

The cross-correlation method is another method of determining a small displacement of the human body (S. Yagi and K. Nakayama, "Local Displacement Analysis of Inhomogenous Soft Tissue by 2-Dimensional Analytic Signal Correlation", Proceedings of the 54th meeting on the Japan Society of Ultrasonics in Medicine, 54-116, pp. 359-360 (May, 1989) (reference [2]).

The cross-correlation method disclosed in reference [2] applies many pulse ultrasonic beams in various directions in the human body, obtains signals corresponding to two tomograms and determines the two-dimensional minute displacement in the human body by calculating a two-dimensional cross-correlation of the signals. The method in reference [2] is also usable in calculating the minute displacement with respect to the depth direction parallel to the scanning line.

Since the determination of the minute displacement is not the subject matter of the present invention, and the cross-correlation method and the pulse Doppler methods are well-known techniques, the description of a method of determining the minute displacement will be omitted.

The subject matter of the present invention is to display the minute displacement determined by the foregoing known methods in a manner useful for diagnosis.

FIGS. 7(A), 7(B) and 7(C) are views of assistance in explaining prior art displaying methods.

FIG. 7(A) is an illustration of a picture displayed by the displaying methods stated in reference [1], in which depth along a scanning line in a tomogram 10 of the human abdomen, having the shades of the diaphragm 11 and a blood vessel 12 is measured on the horizontal axis, minute displacement on the scanning line determined by the prior art method is measured on the vertical axis, and time is measured to an axis perpendicular to a plane defined by the horizontal axis and the vertical axis. It is impossible to recognize all of the minute displacements of the points on the cross section at a glance in the tomogram.

Another displaying method determines the minute displacement of each of the points in a tomogram 10 (each point is represented by a point a) at a moment in which a frame showing the tomogram 10 is formed, represents the minute displacement by a luminance, a value or a chrome of a color, or color variation (hereinafter referred to as "luminance or the like") as shown in FIG. 7(B), superposes the minute displacement of each point represented by a luminance or the like on the tomogram in each frame, and displays frames sequentially as shown in FIG. 7(C).

However, since each point on human body organs moves within a very small time frame, for example, in accordance with a heartbeat, the minute displacement of each point in the tomogram changes very quickly. Therefore, it is difficult to find, or possible to fail in finding an abnormal minute displacement of a point appearing in the tomogram for the diagnosis of a tumor or the like. Therefore, diagnosis using the tomogram requires great skill.

The Doppler method (reference [1]) and the two-dimensional cross correlation (reference [2]) method are representative prior art methods of determining the displacement of each part.

While the Doppler method has the advantages that a displacement can be calculated by the operation of a relatively small operation quantity and the tomogram can be displayed in a real-time mode, the Doppler method is able to calculate only a displacement along the direction of scanning lines. While the two-dimensional cross correlation method is able to calculate a two-dimensional displacement, the two-dimensional cross correlation method needs a large operation quantity in calculating the two-dimensional displacement and is unable to display a tomogram in a real-time mode.

SUMMARY OF THE INVENTION

Accordingly, it is a first object of the present invention to provide an ultrasonic diagnostic apparatus capable of objectively and readily understandably displaying the hardness of tissues of human body organs, the velocity and range of propagation of vibrations through tissues, and characteristics and properties of tissues including the magnitude and direction of movement of internal parts of tissues.

A second object of the present invention is to provide an ultrasonic diagnostic apparatus having an excellent real-time processing the capability and the capability of determining and displaying displacement that is effective for diagnosis.

FIGS. 1, 2 and 3 are typical views assisting in explaining means for achieving the first object of the present invention. Although the present invention is not limited to a displaying method and the like illustrated in FIGS. 1, 2 and 3, the present invention will be explained with reference to FIGS. 1, 2 and 3 to facilitate understanding the present invention.

FIG. 1 is a typical view of assistance in explaining an ultrasonic diagnostic apparatus in a first aspect of the present invention. The ultrasonic diagnostic apparatus receives ultrasonic waves applied to, and reflected by, human body organs, creates signals corresponding to the reflected ultrasonic waves, and determines the minute displacements of points in a cross section of the body on the basis of the signals by the Pulse Doppler method shown in reference [1] or the cross correlation method shown in reference [2] or determines the differential of the minute displacement with respect to the scanning direction, i.e., the direction of depth of the body. Since the differential is substantially equivalent in effect to the minute displacement in explaining the present invention, the differential and the minute displacement will be inclusively referred to as "minute displacement" or simply as "displacement".

Then, the local maximum of the time-dependent variable minute displacement of each point a in the cross section as shown in FIG. 1(A) is determined. The local maximums of the minute displacements of points in the cross section will appear in different frames, i.e., at different times, respectively. For example, the local maximums of the minute displacements of points in the cross section are determined in a time interval between one heartbeat and the next heartbeat. FIG. 1(B), which is similar to FIG. 7(C), shows the varying displacement of each point displayed in a corresponding luminance in sequential frames. The ultrasonic diagnostic apparatus in the first aspect of the present invention displays the local maximum of the varying minute displacement of each point in corresponding luminance or the like as shown in FIG. 1(C).

FIG. 2 is a typical view of assistance in explaining an ultrasonic diagnostic apparatus in a second aspect of the present invention for achieving the first object.

The ultrasonic diagnostic apparatus in the second aspect of the present invention, similarly to the ultrasonic diagnostic apparatus in the first aspect of the present invention, determines the minute displacements of points a, b, c, . . . and d on the basis of signals corresponding to reflected ultrasonic waves, and then, as shown in FIG. 2(A), determines times $\tau a, \tau b, \tau c, \ldots$ and $\tau d$ when the temporal local maximums of the minute displacements of the points a, b, c, . . . and d appear in a time interval between predetermined times, for example, in a time interval between two successive heartbeats. The times $\tau a, \tau b, \tau c, \ldots$ and $\tau d$ correspond, respectively, to times required by a vibration produced by a prescribed portion in the body, for example, the heart, for propagation to the points a, b, c, . . . and d.

FIG. 2(B) shows pictures of the times when the temporal local maximums of the minute displacements of the points appear, respectively, by corresponding luminances as shown in FIG. 2(A), formed in frames 3, 4 and 5 created, respectively, at the times $\tau a, \tau b, \tau c, \ldots$ and $\tau d$ shown in FIG. 2(A). In frame 3, only the time $\tau a$ for the point a is displayed and the times $\tau b, \tau c, \ldots$ and $\tau d$ for the points b, c, . . . and d are not displayed because the local maximums of the minute displacements of the points b, c, . . . and d have not been determined. In frame 4, the times $\tau a$ and $\tau b$ for the points a and b are determined and displayed. In frame 5, the times $\tau a, \tau b$ and $\tau c$ for the points a, b and c are determined and displayed. FIG. 2(C) shows a final picture showing the respective times of all the points in the cross section.

Thus, the ultrasonic diagnostic apparatus in the second aspect of the present invention displays the times $\tau a, \tau b, \tau c, \ldots$ and $\tau d$ thus determined.

FIG. 3 is a typical view of assistance in explaining an ultrasonic diagnostic apparatus in a third aspect of the present invention for achieving the first object.

The ultrasonic diagnostic apparatus in the third aspect of the present invention and an ultrasonic diagnostic apparatus in a fourth aspect of the present invention, similarly to those in the first and second aspects of the present invention, determine the minute displacements of points a, b, c, . . . and d in a cross section on the basis of signals corresponding to reflected ultrasonic waves, determine, similarly to the ultrasonic diagnostic apparatus in the second aspect of the present invention, times $\tau a, \tau b, \tau c,$ and $\tau d$ when the local maximums of the minute displacements of the points a, b, c, . . . and d appear as shown in FIG. 2(A), the times $\tau a, \tau b, \tau c, \ldots$ and $\tau d$ are assigned, respectively, to the points a, b, c, . . . and d, two-dimensional gradients in the picture when the times $\tau a, \tau b, \tau c, \ldots$ and $\tau d$ are used as picture element data, and the gradients at the points at the times are displayed.

The two-dimensional gradient $\nabla t(x, y)$ is represented by the following equation of:

$$\nabla t(x, y) = \frac{\partial \tau(x, y)}{\partial x} ii + \frac{\partial \tau(x, y)}{\partial y} jj$$

wherein (x, y) is the two-dimensional coordinates in the cross section, $\tau(x, y)$ is the time when the temporal local maximum of the minute displacement of the point (x, y) occurs, ii is the unit vector of x direction and jj is the unit vector of y direction.

FIG. 3(A) is a vector representation of the gradients indicated by arrows, and FIG. 3(B) shows streamlines along the gradients at the points in the cross section. Thus, the ultrasonic diagnostic apparatus in the third aspect of the present invention displays the gradients at the points in a cross section.

The illustration of the ultrasonic diagnostic apparatus in the fourth aspect of the present invention is omitted. The ultrasonic diagnostic apparatus in the fourth aspect of the present invention, similarly to the ultrasonic diagnostic apparatus explained with reference to FIG. 3, determines gradients at points in a cross section, determines the magnitudes of the gradients represented by vectors corresponding to the information of the directions of the gradients by mapping, and then displays the magnitudes in corresponding luminances.

The magnitude or the absolute magnitude of the gradient is represented by the equation:

$$|\nabla t(x, y)| = \sqrt{\left[\frac{\partial \tau(x, y)}{\partial x}\right]^2 + \left[\frac{\partial \tau(x, y)}{\partial y}\right]^2}$$

FIGS. 3(C) and 3(D), similarly to FIG. 3(A), show a picture produced by superposing the arrows representing gradients at the points and the local maximums of the displacements of the points (FIG. 1(C)), and a picture produced by superposing the arrows representing the gradients at the points and the times when the local maximums of the displacements of the points appear (FIG. 2(C)), respectively. FIG. 3(E) shows two-dimensional color bars intended to display the local maximums of the displacements of the points (FIG. 1(C))

and the times when the local maximums of the displacements of the points appear (FIG. 2(C)) represented by two factors among the foregoing luminance and the like, including chrome and value and the like. Thus, the present invention may coincidentally display some of the local maximums, the times when the local maximums appear, the gradients and the magnitudes of the gradients, or may coincidentally display some of these variables and variables other than those variables on a screen.

The ultrasonic diagnostic apparatus in the first aspect of the present invention determines the local maximums of minute displacements or the like and displays the local maximums, for example, as shown in FIG. 1(C). Accordingly, the ultrasonic diagnostic apparatus enables instantaneous acquisition of information useful for making a diagnosis, without requiring any great skill. For example, a region where the local maximums are smaller as compared with those in the surrounding regions indicates that tissues in the region are indurated.

The ultrasonic diagnostic apparatus in the second aspect of the present invention determines the times when the local maximums of the minute displacements appear and displays the times, for example, in a picture as shown in FIG. 2(C) to enable the instantaneous recognition of points where the range of propagation of vibrations or the mode of propagation of vibrations is abnormal, as compared with that in the surrounding points. For example, a point where the velocity of propagation of vibrations is high indicates that the tissue at the point is indurated. Thus, the ultrasonic diagnostic apparatus, similarly to that in the first aspect of the present invention, enables the instantaneous acquisition of information useful for diagnosis without requiring any great skill.

The ultrasonic diagnostic apparatus in the third aspect of the present invention determines the gradients of the times when the local maximums of the minute displacements appear, and displays the gradients, for example, in pictures as shown in FIGS. 3(A) and 3(B), which enables the direction and magnitude of movement of tissue to be readily recognized and enables a point where the direction and magnitude of movement of tissue are abnormal, compared with those in the surrounding points, to be readily found.

When the directions of the gradients are indicated by arrows or streamlines, it is impossible to display the gradients minutely over the entire area of the screen; the gradients are displayed discretely, for example, as shown in FIGS. 3(A) and 3(B). On the other hand, the ultrasonic diagnostic apparatus in the fourth aspect of the present invention enables the distribution of velocities of propagation of vibrations to be recognized instantaneously by minutely displaying the magnitudes of the gradients over the entire area of the screen, so that even a small abnormal point will not be overlooked and can be easily found.

Thus, the ultrasonic diagnostic apparatuses of the present invention, as compared with the prior art ultrasonic diagnostic apparatus (FIG. 7) that displays the displacements of points occurred at certain time, displays more intelligibly the characteristics and properties of tissues, such as the maximum displacement and hardness of tissues, the velocity of propagation of vibrations through tissues, and the direction and magnitude of movement of tissues.

The ultrasonic diagnostic apparatus in a fifth aspect of the present invention invented to achieve the second object of the present invention creates original data from ultrasonic waves applied to and reflected by human body organs, and displays a tomogram produced on the basis of the data. This ultrasonic diagnostic apparatus comprises:

(1) a specifying unit for specifying at least one desired point and at least one desired direction in a tomogram displayed on a screen;
(2) a data generating unit for generating calculating data along a line segment passing a desired point and extending in a desired direction, on the basis of the original data, for a plurality of tomogram obtained, respectively, at different times;
(3) a calculating unit for calculating information on the basis of the displacements of desired points along the desired direction or the respective rates of change of the displacements along the desired direction; and
(4) a display unit for displaying the information.

The calculating unit calculates the displacement or the rate of change of the displacement itself as the information, or calculates one or some of the temporal local maximum in the displacement or the rate of change of the displacement, the time corresponding to the temporal local maximum, the gradient of the time and the magnitude of the gradient as the information.

The specifying unit specifies a plurality of desired directions or specifies one or a plurality of desired directions among a plurality of predetermined directions.

The specifying unit specifies a run of a plurality of desired points forming a line along the desired direction or may specify a plurality of desired points in a two-dimensional arrangement.

The data generating unit may generate calculating data by interpolating between the original data or extracts, if the data generating unit is provided additionally with an interpolating unit for carrying out interpolation for the entire area of a screen, specific calculating data from the data obtained by interpolation.

When the ultrasonic diagnostic apparatus is used, for example for the examination of the liver, the parenchyma of the lives moves in synchronism with the heartbeat and a large displacement of the parenchyma of the lives occurs only in a fixed direction. Accordingly, satisfactory data can be obtained through the observation of the displacement of the parenchyma only along the fixed direction. The ultrasonic diagnostic apparatus of the present invention was made on the basis of such a fact. The ultrasonic diagnostic apparatus of the present invention specifies desired points and a desired direction on a tomogram (unit stated in (1)), generates calculating data passing a desired point along the desired direction by interpolating between the original data, for a plurality of tomograms obtained, respectively, at different times (unit stated in (2)), calculates the displacements of the desired points along the desired direction or the respective rates of change of the displacements on the basis of the calculating data (unit stated in (3)), and displays the calculated displacements or the rates of change of the displacements (unit stated in (4)). Thus, the ultrasonic diagnostic apparatus is capable of calculating the displacements by one-dimensional operation of a relatively small operation quantity, of displaying the displacements in a real-time mode and of providing displacements along a desired direction effective for diagnosis.

The ultrasonic diagnostic apparatuses in the first to fourth aspect of the present invention calculates minute displacements or the like, or calculate, in addition to the minute displacements, the respective local maximums of the displacements varying with time, times when the local maximums appear, the gradients of the times, and the absolute magnitudes of the gradients, and display those calculated values instead of simply displaying the calculated minute displacements occurring at times. Accordingly, the characteristics and properties of tissues including the hardness of tissues, the velocity of propagation of vibrations, and the magnitude and direction of movement of the interior of the tissues can be recognized. Furthermore, the ultrasonic diagnostic apparatuses display the characteristics and properties of the tissues in a visually intelligible picture by using luminances, values of color, chroma or vectors corresponding to the calculated data.

The ultrasonic diagnostic apparatus in the fifth aspect of the present invention specifies desired points and a desired direction on a tomogram, generates calculating data by interpolating between the original data, for a plurality of tomograms obtained, respectively, at different times, determines the information on the basis of the displacements of the desired points along the desired direction or on the basis of the rates of change of the displacements of the desired points along the desired direction on the basis of the calculating data, and displays the information. The displacement itself, the rate of change of the information itself, the temporal local maximum in the displacement or the rate of change of the displacement, the time corresponding to the temporal local maximum, the gradient of the time and the magnitude of the gradient are usable as the information. Accordingly, the diagnostically effective displacements of the desired points can be displayed in a real-time mode by one-dimensional operation of a relatively small operation quantity.

BRIEF DESCRIPTION OF THE DRAWINGS

FIG. 13, a composite of parts (a) and (b), also variously and respectively referred to herein as FIGS. 13(a) and 13(b), presents graphs of assistance in explaining the function of a very-low-frequency component removing means.

DESCRIPTION OF THE PREFERRED EMBODIMENTS

Preferred embodiments of the present invention will be described hereinafter with reference to the accompanying drawings.

Figure 4:
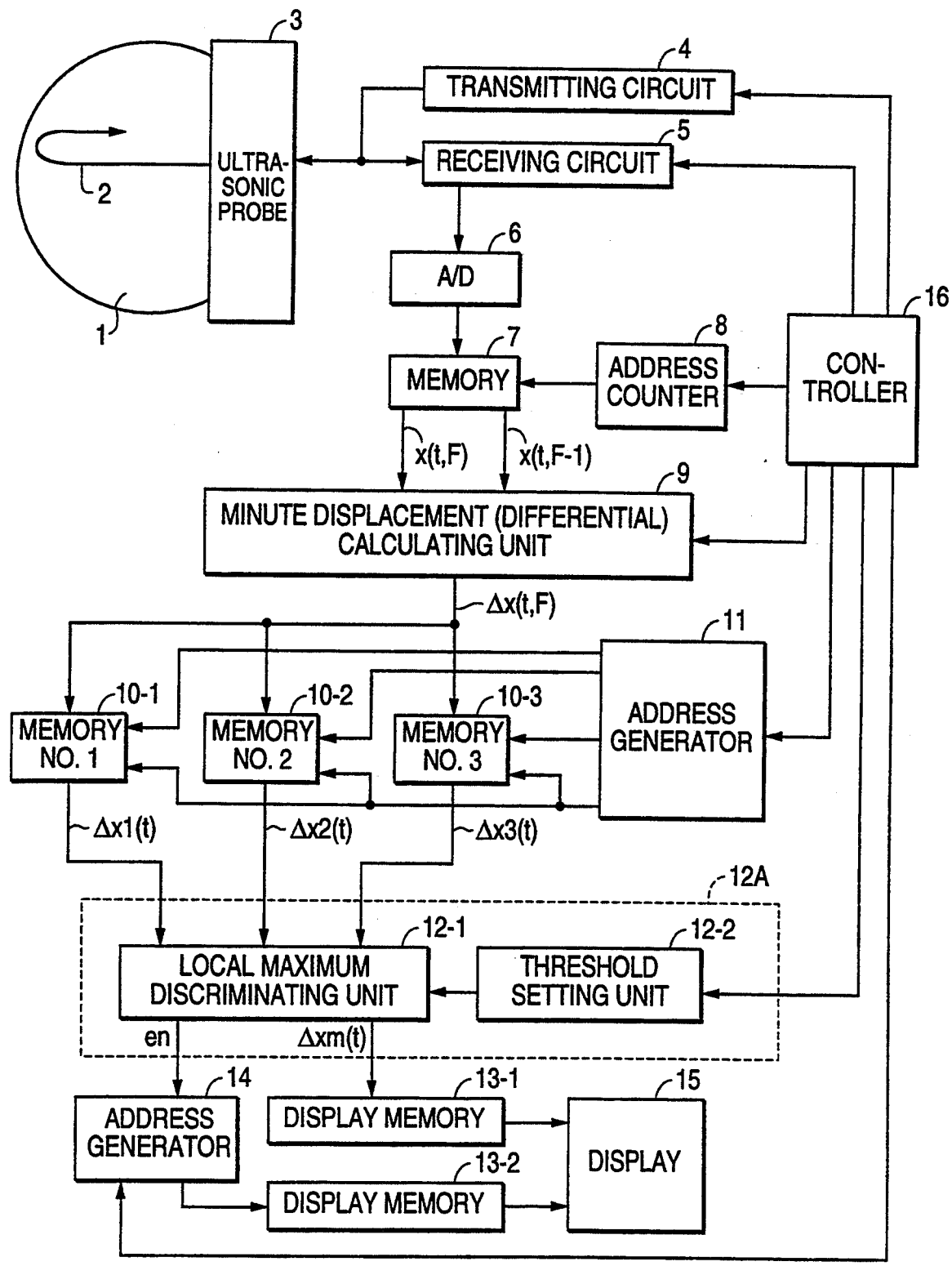
FIG. 4 is a block diagram of the ultrasonic diagnostic apparatus in the first embodiment.

Referring to FIG. 4, which shows a block diagram of an ultrasonic diagnostic apparatus in a first embodiment according to the present invention, a controller 16 sends a transmission control signal to a transmitting circuit 4, and then the transmitting circuit 4 sends a transmission signal to an ultrasonic probe 3. The ultrasonic probe 3 converts the transmission signal into an ultrasonic wave 2 and sends the ultrasonic wave 2 into the body 1. The ultrasonic probe 3 receives the reflected ultrasonic wave 2 reflected by the internal tissues of the body 1 and converts the same into data signal. A receiving circuit 5 receives the data signal and subjects the same to delaying and addition for dynamic focusing and scanning, under the control of the controller 16. The delayed and added data signals are converted into proportional digital data by an A/D converter 6 and the digital data is stored temporarily in a memory 7. In storing the digital data, the controller 16 sends a control signal to an address counter 8 to control the address counter 8 to allocate an address to each piece of data X(t, F) representing a frame F and time t in the frame F.

Then, data X(t, F) of a frame F and data X(t, F−1) of the preceding frame F−1 are transferred from the memory 7 to a minute displacement (differential) calculating unit 9. Then, the minute displacement (differential) calculating unit 9 calculates the minute displacement of each point in a cross section with respect to the scanning direction or the differential of the minute displacement of each point with respect to the direction of depth (hereinafter referred to simply as "minute displacement") $\Delta X(t, F)$.

The minute displacement ΔX(t, F) may be calculated by any suitable method, such as a cross correlation method or a pulse Doppler method.

The controller 16 gives instructions to an address generator 11 to control the minute displacement ΔX(t, F) calculated by the minute displacement (differential) calculating unit 9 to store the minute displacements ΔX(t, F), as F runs from 1 to n sequentially and recurrently in memories 10-1, 10-2 and 10-3, in that order.

Corresponding pixel data ΔX1(t), ΔX2(t) and ΔX3(t), among the data representing the minute displacements ΔX(t, F) in three frames, are read simultaneously from the three memories 10-1, 10-2 and 10-3, and then the pixel data are applied to a local maximum discriminating unit 12-1 included in a local maximum calculating unit 12. A threshold setting unit 12-2 gives a threshold Th to the local maximum discriminating unit 12-1. Then, the local maximum discriminating unit 12-1 compares the three input data ΔX1(t), ΔX2(t) and ΔX3(t) of each pixel in the successive three frames F−1, F and F+1, and determines that the data ΔX2(t) for the middle frame F with respect to time is a local maximum ΔXm(t) when the data ΔX2(t) meets inequalities:

$$\Delta X1(t) \leq \Delta X2(t) - Th$$

$$\Delta X3(t) \leq \Delta X2(t) - Th \quad (1)$$

Then, the data of the next frame is stored in the memory storing the data of the earliest frame among the memories 10-1, 10-2 and 10-3. The data for the three successive frames F, F+1 and F+2 are subject to the discrimination of the local maximum.

Figure 1A:
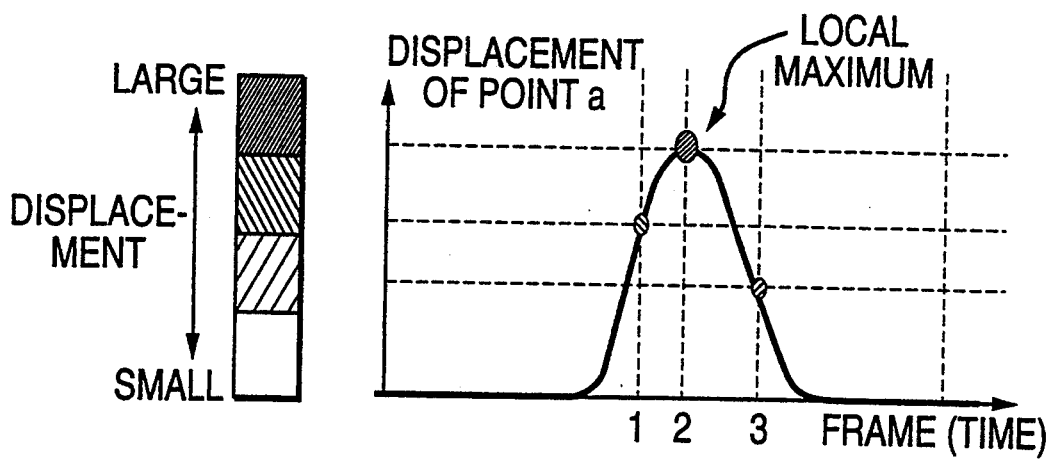
FIG. 1, a composite of parts (A), (B) and (C), also variously and respectively referred to herein as FIGS. 1(A), 1(B) and 1(C), presents typical views of assistance in explaining an ultrasonic diagnostic apparatus in a first embodiment according to the present invention.
Figure 1B:
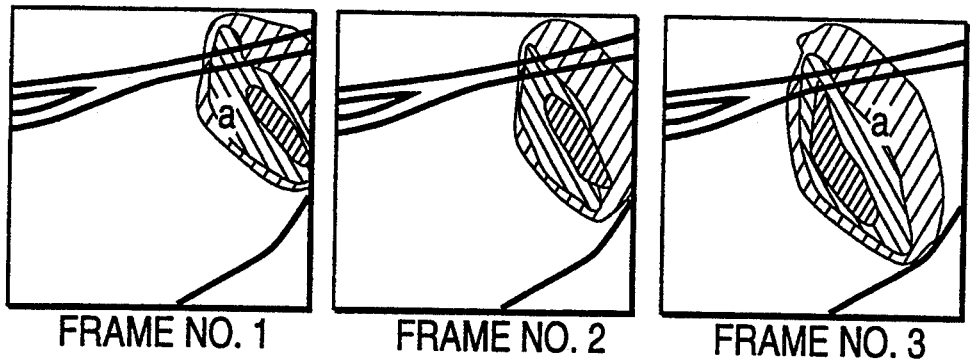
Figure 1C:
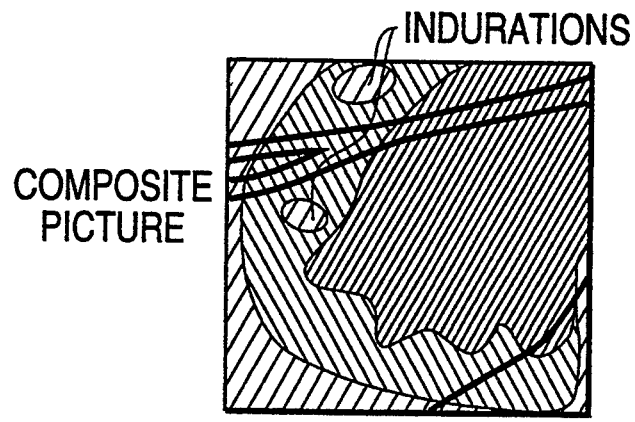

The local maximum ΔXm(t) discriminated by the local maximum discriminating unit 12-1 is stored in a display memory 13-1 and an enable signal (en) indicating the discrimination of the local maximum ΔXm(t) is given to an address generator 14. The address generator 14 allocates an addresses (a position in the cross section) to the local maximum ΔXm(t) and stores the address in a display memory 13-2. After thus accumulating the local maximums ΔXm(t) at points in the cross section at each time, and their addresses respectively, in the display memories 13-1 and 13-2, the data representing the local maximums ΔXm(t) are transmitted to a display 15 to display a picture of pixels having luminances proportional, respectively, to the local maximums ΔXm(t) as shown in FIG. 1(C) on the screen of the display 15.

The display 15 may display momentarily the pictures representing the minute displacements varying with time in addition to the picture representing the local maximums ΔXm(t) calculated by the local maximum calculating unit 12.

Figure 5:
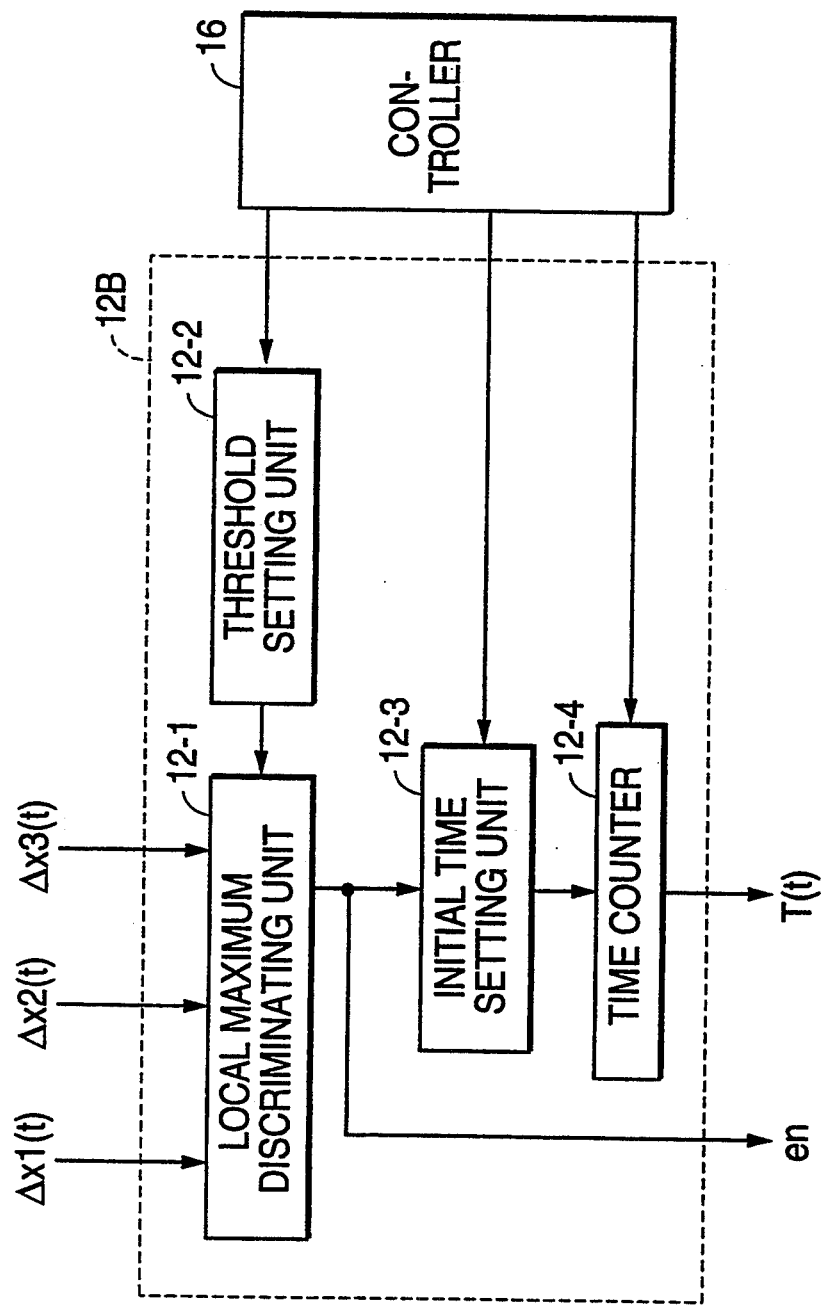
FIG. 5 is a block diagram of a portion of the ultrasonic diagnostic apparatus in the second embodiment, differing from the ultrasonic diagnostic apparatus shown in FIG. 4.

FIG. 5 shows an ultrasonic diagnostic apparatus in a second embodiment according to the present invention, which is similar to the ultrasonic diagnostic apparatus in the first embodiment shown in FIG. 4 and hence only a portion different from the ultrasonic diagnostic apparatus in the first embodiment is shown in FIG. 5. The ultrasonic diagnostic apparatus in the second embodiment is provided with a local maximum time calculating unit 12B instead of the local maximum calculating unit 12A shown in FIG. 4. Only the local maximum time calculating unit 12B will be described hereinafter.

Referring to FIG. 5, a local maximum discriminating unit 12-1 included in the local maximum time calculating unit 12B, similarly to the local maximum discriminating unit 12-1 of the FIG. 4, discriminates a local maximum ΔXm(t), and provides an enable signal (en) when a local maximum ΔXm(t) is found. An initial time setting unit 12-3 determines time when a frame, for which a largest number of enable signals are provided corresponding to a plurality of points on a spatially fixed scanning line, is produced among frames successively applied thereto, as initial time; that is, time when the movement of a point in a cross section caused by, for example, a heartbeat reaches a maximum is used as initial time. Heartbeats may be detected by an external detector and the initial time may be time when a heartbeat is detected. A time counter 12-4 is cleared at each initial time.

Figure 2A:
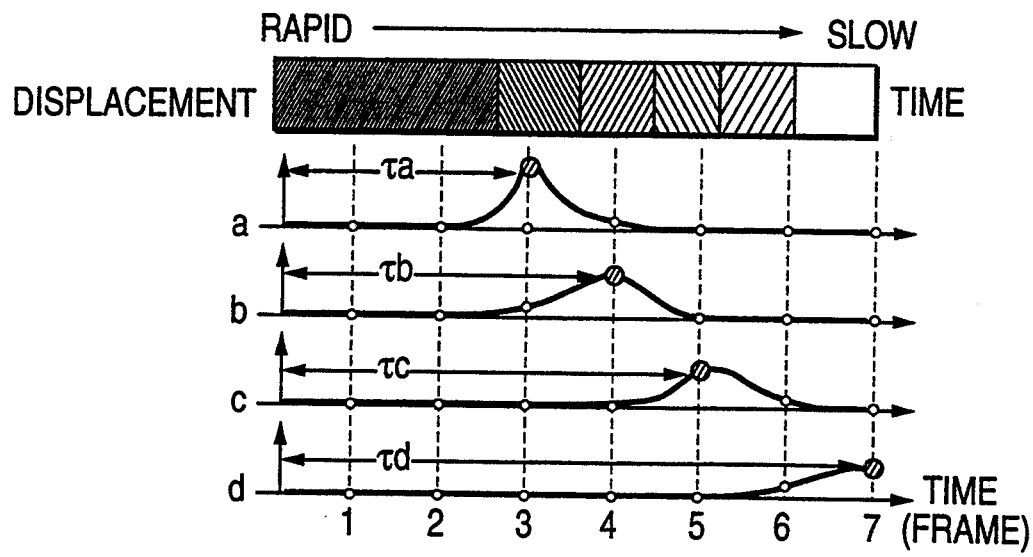
FIG. 2, a composite of parts (A), (B) and (C), also variously and respectively referred to herein as FIGS. 2(A), 2(B) and 2(C), presents typical views of assistance in explaining an ultrasonic diagnostic apparatus in a second embodiment according to the present invention.
Figure 2B:
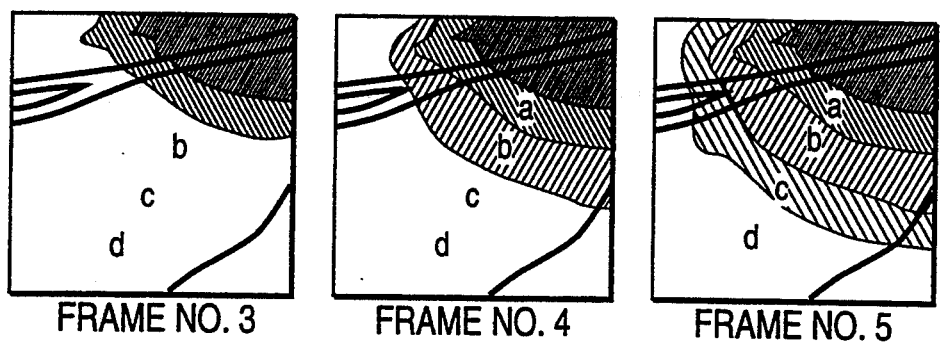
Figure 2C:
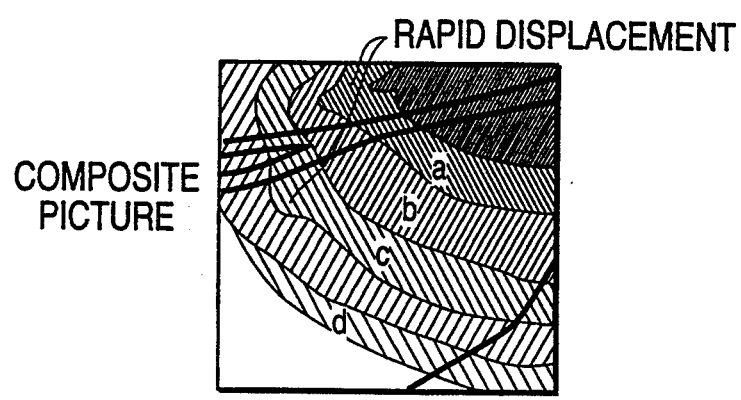

When a local maximum is found and an enable signal is provided, the local maximum calculating unit 12A applies the enable signal (en) and time T(t) when the enable signal (en) is provided to the display memory 13-1 and the address generator 14 shown in FIG. 4, and then a picture of pixels of luminances proportional to the times T(t) coinciding with the local maximums accumulated in the display memories 13-1 and 13-2 (FIGS. 2(B) and 2(C)) is displayed on the display 15.

The ultrasonic diagnostic apparatus may be provided with a correcting unit for correcting the time difference between the reception of an echo from a point corresponding to one end of the screen and the reception of an echo from a point corresponding to the other end of the screen in calculating the time.

Figure 6:
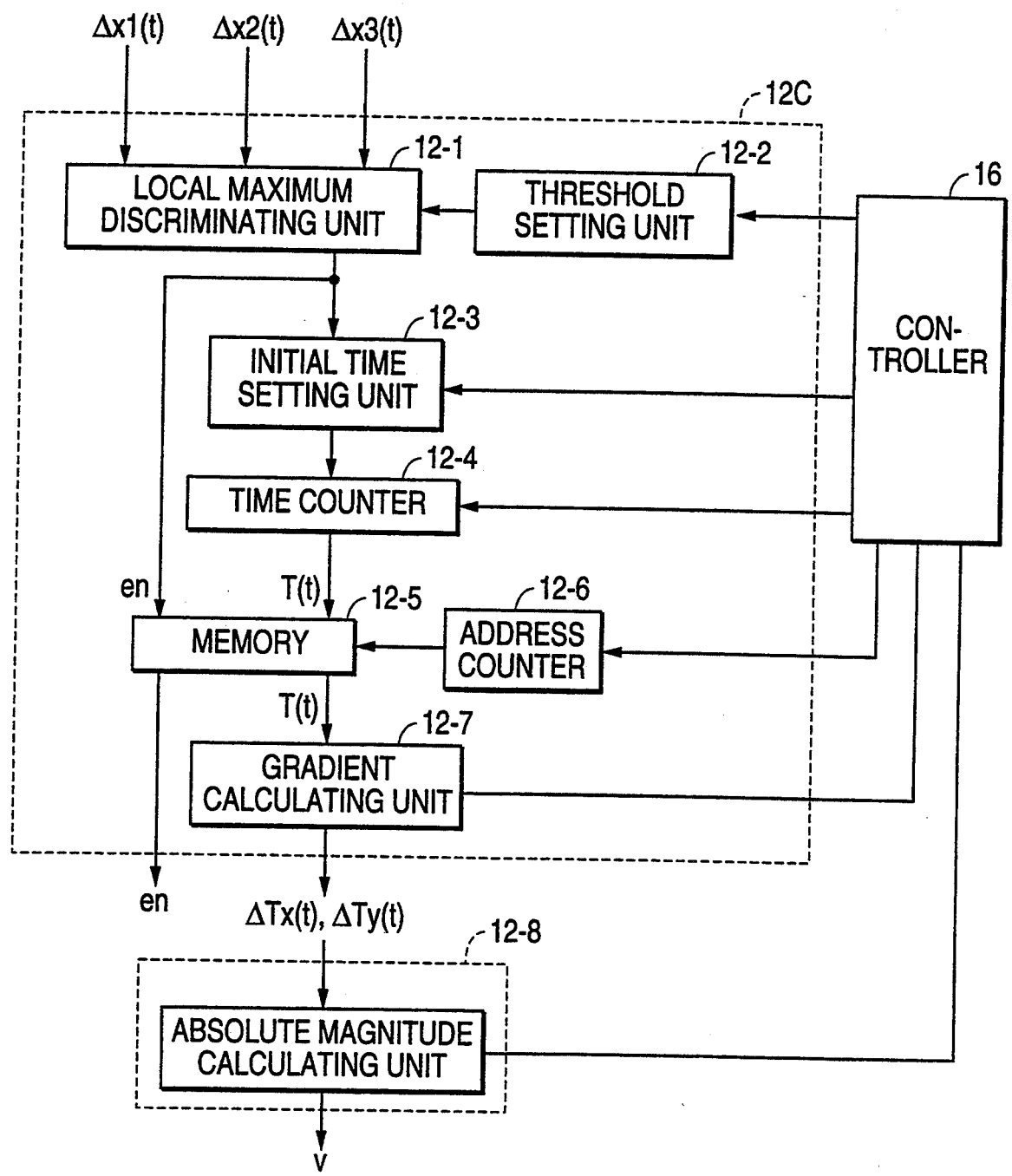
FIG. 6 is a block diagram of a portion of the ultrasonic diagnostic apparatus in the third embodiment, differing from the ultrasonic diagnostic apparatus shown in FIG. 4.
Figure 7A:
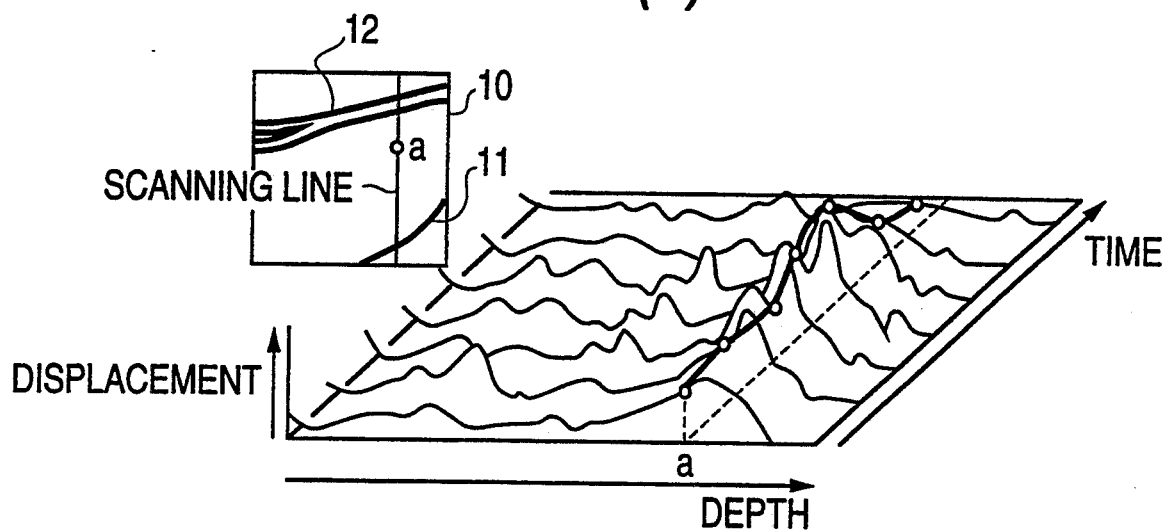
FIG. 7, a composite of parts (A), (B) and (C), also variously and respectively referred to herein as FIGS. 7(A), 7(B) and 7(C), presents pictorial views of assistance in explaining a prior art displaying method.
Figure 7B:
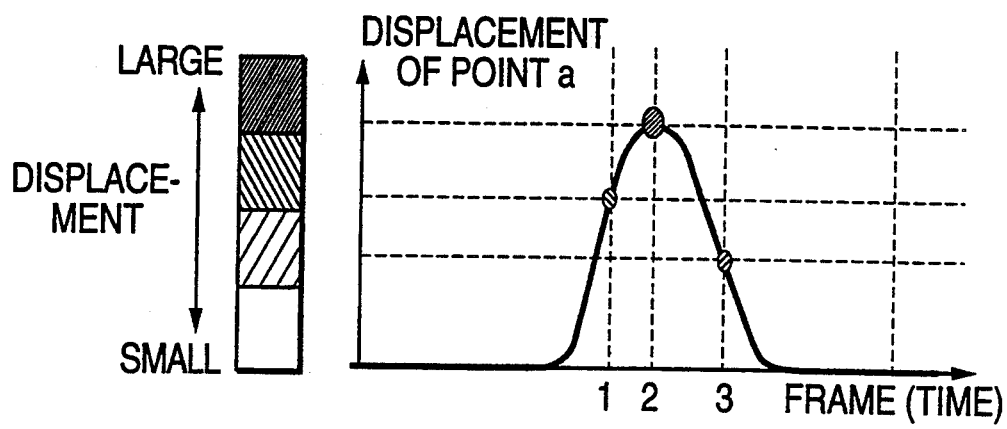
Figure 7C:
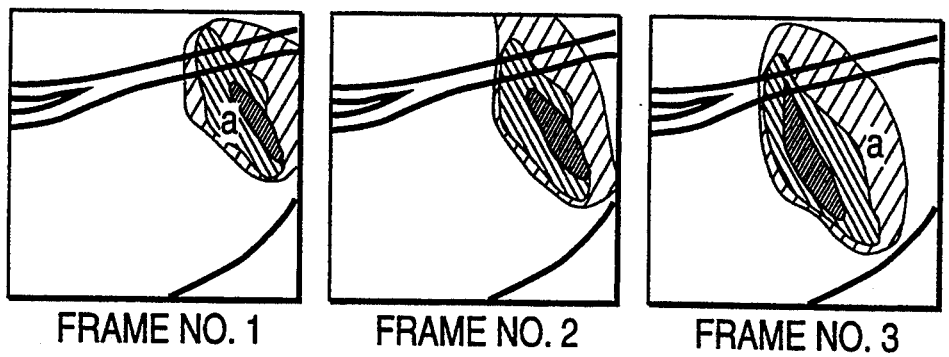

FIG. 6 shows a portion of an ultrasonic diagnostic apparatus in a third embodiment according to the present invention that is different from the ultrasonic diagnostic apparatus in the first embodiment shown in FIG. 4. The ultrasonic diagnostic apparatus in the third embodiment is provided with a gradient calculating unit 12C instead of the local maximum calculating unit 12A.

A local maximum discriminating unit 12-1 and a threshold setting unit 12-2 included in the gradient calculating unit 12C are the same in function as those shown in FIGS. 4 and 5, an initial time setting unit 12-3 and a time counter 12-4 included in the gradient calculating unit 12C are the same in function as those shown in FIG. 5, and hence the description thereof will be omitted.

Times T(t) corresponding to the local maximums of points, provided by the time counter 12-4 in synchronism with enable signals (en) provided by the local maximum discriminating unit 12-1 are stored according to address information provided by an address counter 12-6 in a memory 12-5. Thus, a picture represented by pixel data corresponding to the times T(t) is stored in the memory 12-5. Then, the times T(t) read from the memory 12-5 are applied to a gradient computing unit 12-7. The gradient computing unit 12-7 calculates differentials with respect to an x-direction and a y-direction perpendicular to the x-direction on the picture to determined a gradient (ΔTx(t), ΔTy(t)) for each pixel. The gradient is sent out together with the enable signal (en) from the memory 12-5.

Figure 3A:
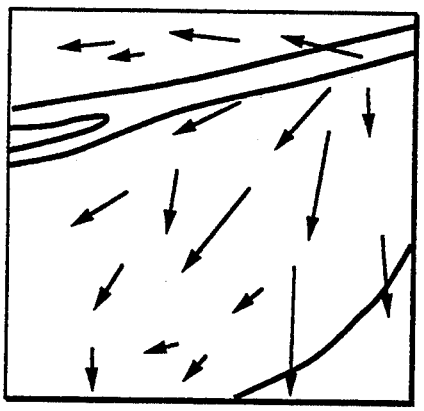
FIG. 3, a composite of parts (A), (B), (C), (D) and (E), also variously and respectively referred to herein as FIGS. 3(A), 3(B), 3(C), 3(D) and 3(E), presents typical views of assistance in explaining an ultrasonic diagnostic apparatus in a third embodiment according to the present invention.
Figure 3B:
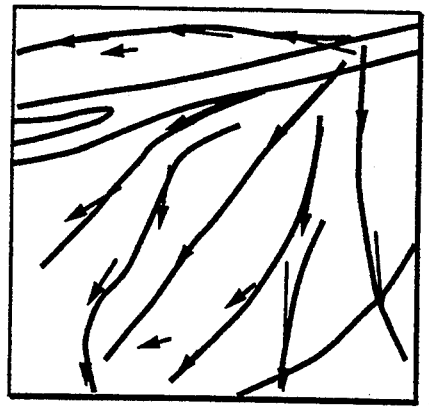
Figure 3C:
Figure 3D:
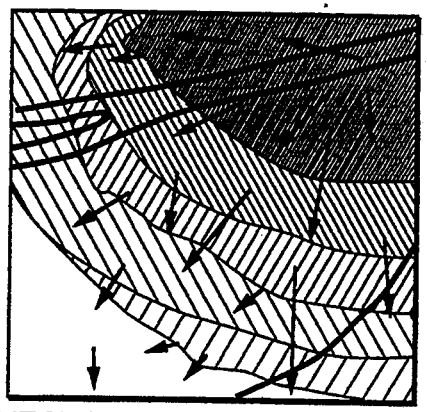
Figure 3E:
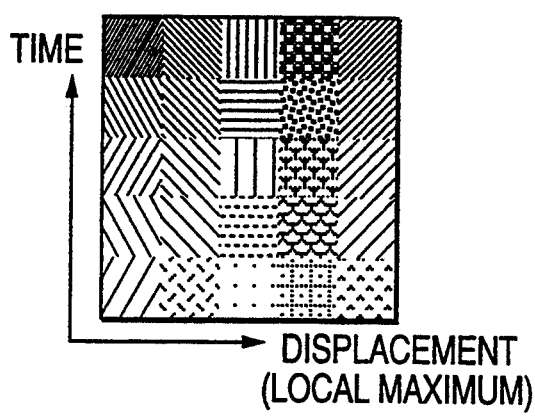

When it is desired to display the gradients (ΔTx(t), ΔTy(t)) in a picture as shown in FIG. 3(A) or 3(B) on the display 15 shown in FIG. 4, the gradients read from the gradient computing unit 12-7 and the enable signals (en) provided by the memory 12-5 are applied, respectively, to the display memory 13 and the address generator 14 (FIG. 4).

When it is desired to display the magnitudes of the gradients, an absolute magnitude calculating unit 12-8 calculates the respective absolute magnitudes V of the gradients (ΔTx(t), ΔTy(t)) computed by the gradient computing unit 12-7, and then the absolute magnitudes V and the enable signals (en) are given, respectively, to the display memory 13-1 and the address generator 14 (FIG. 4).

Naturally, any two or three unit among those shown in FIGS. 4, 5 and 6 may be displayed simultaneously.

An ultrasonic diagnostic apparatus in a fifth embodiment according to the present invention will be described hereinafter with reference to FIG. 8.

Figure 8:
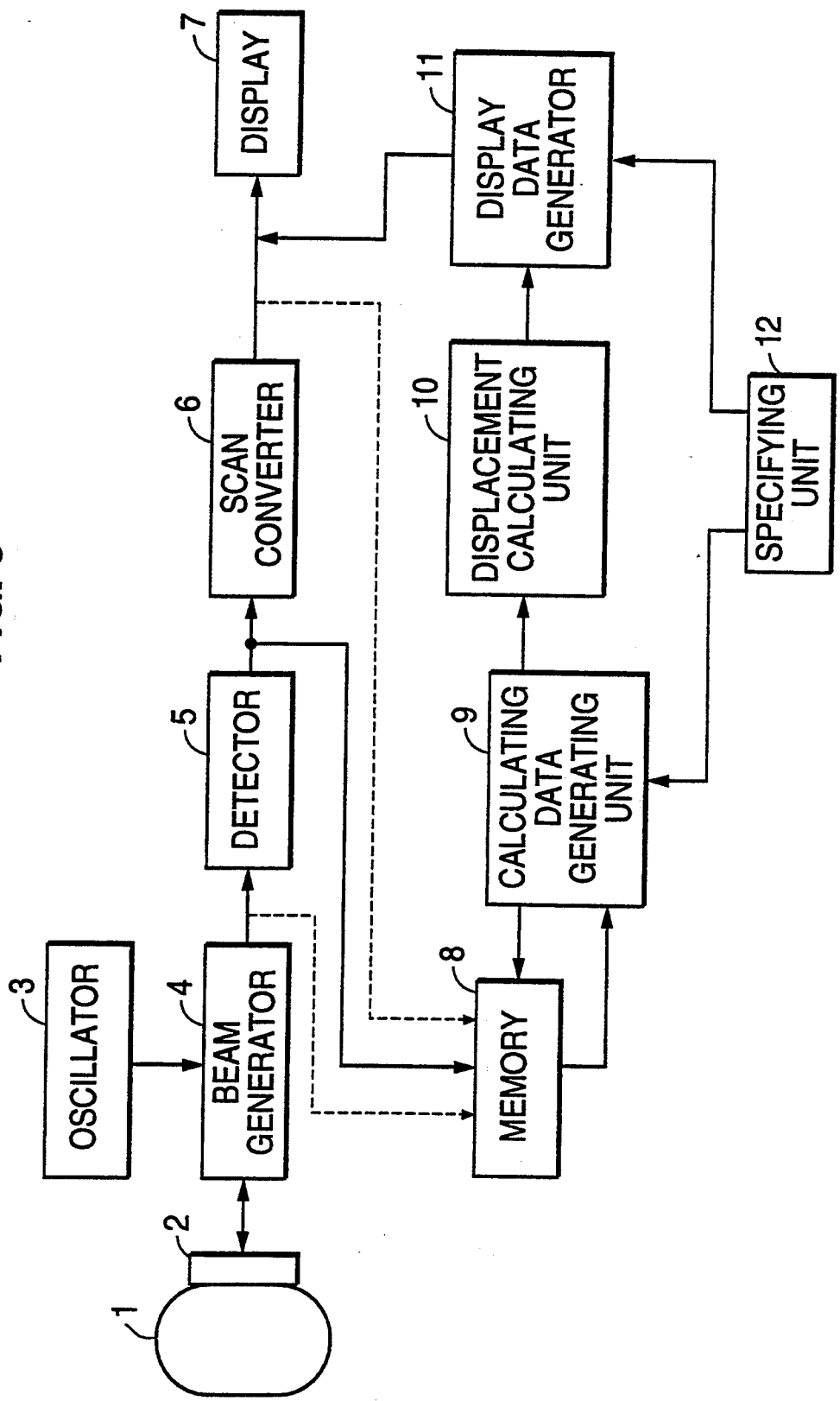
FIG. 8 is a block diagram of an ultrasonic diagnostic apparatus embodying the present invention.

Referring to FIG. 8, an oscillator generates a pulse signal, a beam generator 4 delays the pulse signal so that the pulse signal is focused at a predetermined position within the body 1, the delayed pulse signal is applied to an ultrasonic transducer 2, and then the ultrasonic transducer sends ultrasonic waves into the body 1. The ultrasonic waves are reflected by tissues within the body 1, the reflected ultrasonic waves are received by the ultrasonic transducer 2, and then the ultrasonic transducer 2 generates data signals corresponding to the reflected ultrasonic waves. The beam generator 4 delays and adds the data signals so that the data signals are focused at a predetermined position within the body 1. Then, a detector 5 detects the data signals and the detected data signals are given to a scan converter 6. The scan converter 6 processes the detected data signals for coordinate transformation so that the detected data signals can be displayed on a display 7, and a tomogram of the body is displayed on the display 7. The foregoing operations are the same as those performed by the prior art ultrasonic diagnostic apparatus.

The detected data signals provided by the detector 5 is stored temporarily in a memory 8. A desired point and a desired direction are specified in the tomogram displayed on the display 7 by unit a specifying unit 12 including a pointing device, such as a mouse or a trackball. The desired point and the desired direction specified by the specifying unit 12 is given to a display data generator 11, the display data generator 11 generates display data, and the display data generated by the display data generator 11 is superposed upon the tomogram displayed on the display 7.

Figure 9A:
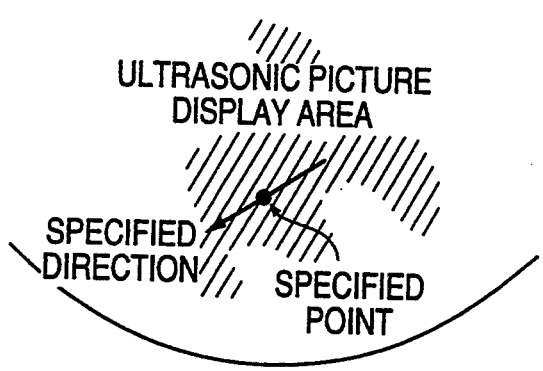
FIG. 9, a composite of parts (a), (b), (c) and (d), also variously and respectively referred to herein as FIGS. 9(a), 9(b), 9(c) and 9(d), presents views of assistance in concretely explaining a method of specifying desired points and desired directions.
Figure 9B:
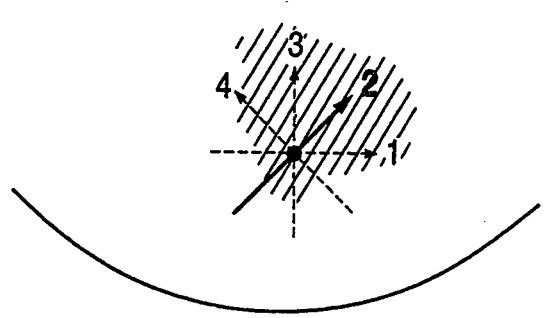
Figure 9C:
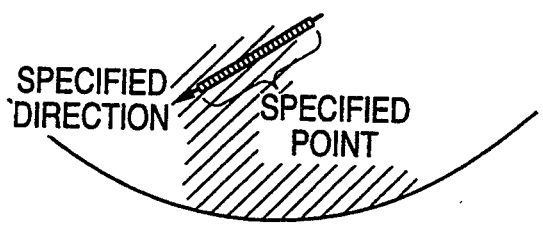
Figure 9D:
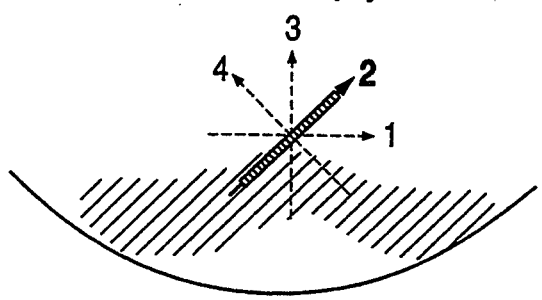
Figure 10E:
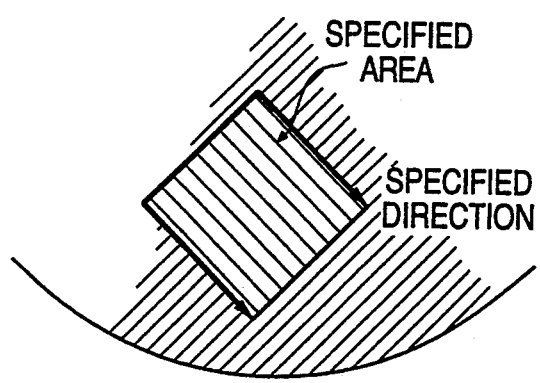
FIG. 10, a composite of parts (e), (f) and (g), also variously and respectively referred to herein as FIGS. 10(e), 10(f) and 10(g), presents views of assistance in concretely explaining a method of specifying desired points and desired directions.
Figure 10F:
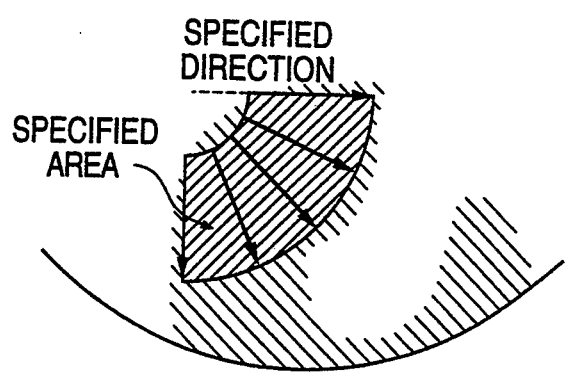
Figure 10G:
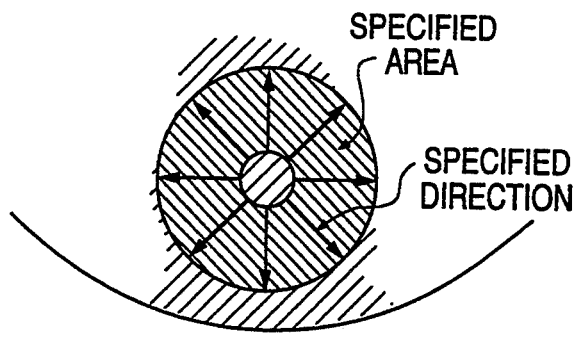

FIGS. 9(a) to 9(d) and 10(e) to 10(g) are views of assistance in explaining a concrete manner of specifying the desired point and the desired direction. FIGS. 9(a) and 9(b) show the specification of a point, FIGS. 9(c) and 9(d) show the specification of a plurality of points on a line segment, and FIGS. 10(e) to 10(g) show the specification of a plurality of directions on an area.

FIG. 9(a) shows, on a picture, a direction and a central point indicated by a solid circle for calculating a displacement. The point and the direction can be optionally changed by unit of a mouse or the like. The central point indicated by a solid circle need not necessarily be displayed.

FIG. 9(b) shows the selection of one of a plurality of predetermined directions indicated by markers. In FIG. 9(b), a direction indicated by a marker No. 2 among the four markers Nos. 1, 2, 3 and 4 is selected.

FIG. 9(c) shows the specification of a plurality of points on a line segment. FIG. 9(d) shows the selection of one of a plurality of markers respectively indicating a plurality of directions, and the specification of a plurality of points on a line segment extending in the direction indicated by the selected marker. A plurality of directions may be specified instead of one.

FIGS. 10(e), 10(f) and 10(g) show the specification of a rectangular area, a sectorial area and an annular area, respectively.

After a desired point or points, and a desired direction or directions have been specified, information representing the desired point or points, and a desired direction of directions is given to a calculating data generator 9. Then, the calculating data generator 9 generates calculating data for determining a plurality of pixels lined on a line segment or line segments passing the desired point or points and extending in the desired direction of directions.

Figure 11B:
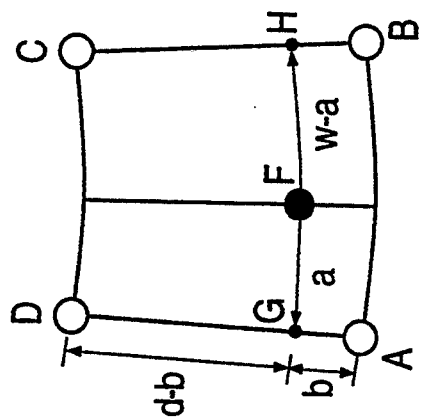
FIG. 11, a composite of parts (a) and (b), also variously and respectively referred to herein as FIGS. 11(a) and 11(b), presents diagrammatic views of assistance in explaining a method of calculating data by a calculating data generating means.
Figure 11A:
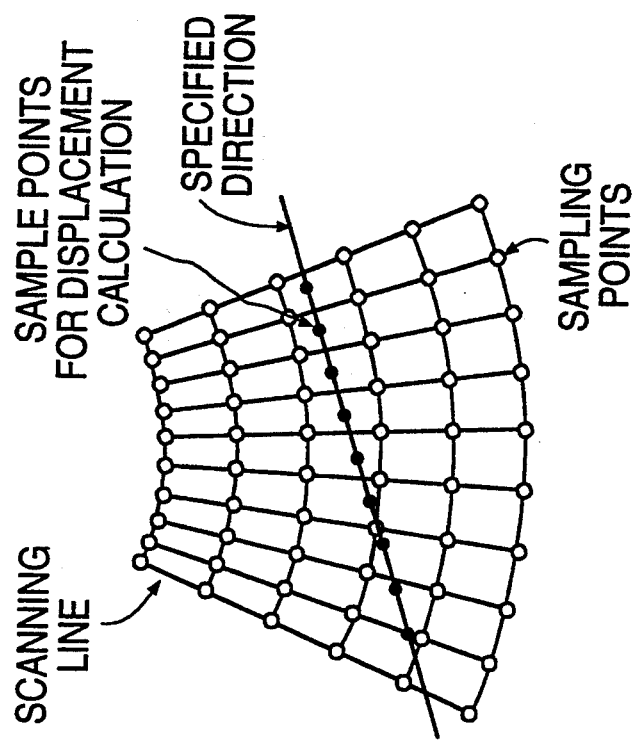

FIGS. 11(a) and 11(b) are views of assistance in explaining the calculating data generating operation of the calculating data generator 9.

Referring to FIG. 11(a), sampling points on ultrasonic scanning lines are indicated by blank circles and data points including the points specified by the specifying unit 12 and lined on a line extending in the specified direction are indicated by solid circles. Data of the data points indicated by solid circles is calculating data. The data points, the data of which is desired to be calculated, do not necessarily coincide with data points on the ultrasonic scanning lines. Accordingly, it is necessary to generate the data of the data points indicated by solid circles on the basis of the data of the sampling points indicated by blank circles.

The calculating data generator 9 generates the data of the data points indicated by solid circles. The data generating operation of the calculating data generator 9 will be described with reference to FIG. 11(b) by way of example. Suppose that calculating data F is generated by using the data of four sampling points indicated by blank circles around a data point indicated by a solid circle. Referring to FIG. 11(b), the distance between the points A and D is d, the distance between the points C and B is also d, the length of a circular arc GFH, where G is the point of intersection of a line segment AD and the circular arc, and H is the point of intersection of a line segment BC and the circular arc, is w. In this example, since sector scanning is assumed, the line between the points G and H is a circular arc. When linear scanning is assumed, the line between the points G and H is a straight line.

The mean of the data of the points A, B, C and D is defined by the following expressions. In the following expressions, the data of the points is represented by the characters indicating the points.

$$G = (d - b)/d * A + b/d * D \qquad (1)$$
$$H = (d - b)/d * B + b/d * C \qquad (2)$$
$$\begin{aligned} F &= (w - a)/w * G + a/w * H \qquad (3)\\ &= (d - b)(w - a)/wd * A + (d - b) a/wd * B +\\ &\quad ba/wd * C + (w - a) b/wd * D \end{aligned}$$

A series of data calculated by using these expressions are represented by $s(r, t)$, in which the argument r indicates a specified direction and t indicates time corresponding to the data.

The calculating data $s(r, t)$ thus generated by the calculating data generator 9 is operated by a displacement calculating unit 10 to determine the displacement of the point specified by the specifying unit 12.

Figure 12:
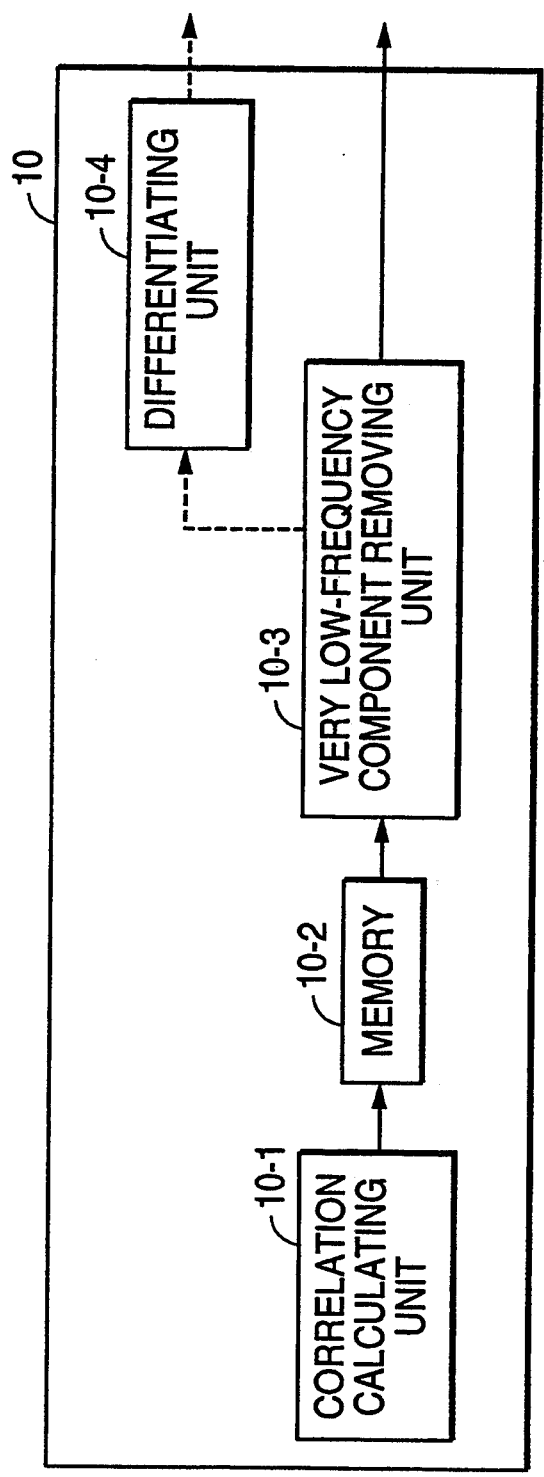
FIG. 12 is a block diagram of a displacement calculating means.

FIG. 12 is a block diagram of the displacement calculating unit 10.

A correlation calculating unit 10-1 operates the calculating data $s(r, t)$ by using the following expression (4)

for calculating cross correlation to determine the displacement.

$$C(\tau) = \Sigma S(r, t1) \cdot (S(r+\tau, t2)) \quad (4)$$

where s(r, t1) is the calculating data at time t1, s(r, t2) is the calculating data at time t2, C($\tau$) is cross correlation function, $-T/2$ to $T/2$ is the range of a space window.

The value of $\tau$ corresponding to the maximum value of C($\tau$) is the displacement.

Displacements are thus determined sequentially for a plurality of frames and the displacements are stored temporarily in a memory 10-2. The displacements are read from the memory 10-2 and operated by a very-low-frequency component removing unit 10-3.

FIGS. 13(a) and 13(b) are graphs of assistance in explaining calculation to be performed by the very-low-frequency component removing unit 10-3.

As shown in FIG. 13(a), the variation of the calculated displacement indicated by a continuous line is the superposition of a slow variation of displacement attributable to breathing or the like and a rapid variation of displacement attributable to the pulsation of the heart. The very-low-frequency component removing unit 10-3 removes the slow variation of displacement attributable to breathing or the like to extract only the displacement attributable to the pulsation of the heart as shown in FIG. 13(b). The displacement calculating unit 10 gives the displacement attributable to the pulsation of the heart, if necessary, after differentiating the same by a differentiating unit 10-4 to the display data generator 11.

The differentiating unit 10-4 processes the thus determined displacement to spatial differentiation with respect to the specified direction (FIG. 10(a)) to determine the gradient of the displacement with respect to the specified direction. The display data generator 11 receives the displacement or the gradient thus determined and generates picture data corresponding to the displacement or the gradient, and then the display 7 displays the picture represented by the picture data.

FIGS. 14(a) to 14(d) are graphs showing the mode of displaying the displacement and the gradient.

Figure 14A:
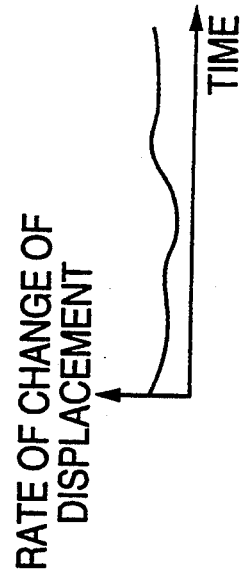
FIG. 14, a composite of parts (a), (b), (c) and (d), also variously and respectively referred to herein as FIGS. 14(a), 14(b), 14(c) and 14(d), presents graphs showing manners of displaying displacement and rate of change of displacement.

FIG. 14(a) shows the variation of the displacement of a specified point with time in the specified direction when only one point is specified as shown in FIGS. 9(a) and 9(b).

Figure 14C:
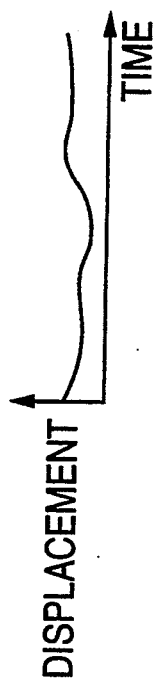
Figure 14B:
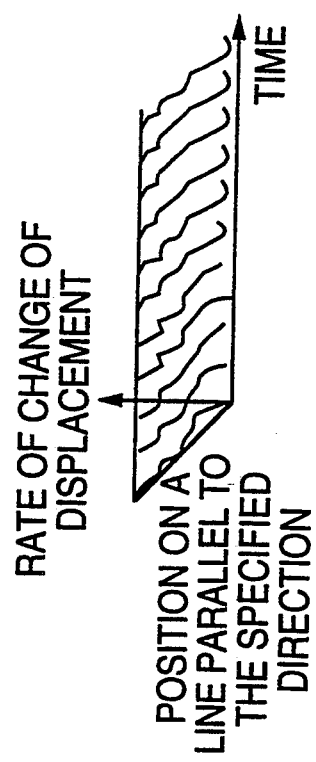

FIG. 14(b) shows a mode of displaying the displacements of a plurality of points lined on a line extending in the specified direction as shown in FIGS. 9(c) and 9(d), in which the variation of the displacement of each specified point with time in the specified direction is displayed in a three-dimensional picture.

When an area is specified as shown in FIG. 10(e), 10(f) or 10(g), the displacement or the gradient may be transformed into color difference signals by a color encoder and the color difference signals may be superposed upon the tomogram.

Figure 14D:
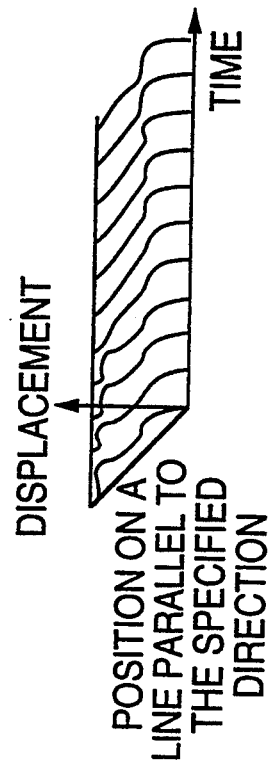

FIG. 14(c) and 14(d) show the variation of the gradient of the displacement with time. FIGS. 14(c) and 14(d) correspond, respectively, to FIGS. 14(a) and 14(b).

Thus, a direction is specified optionally, the displacement or the gradient with respect to the specified direction is calculated and the calculated displacement or the calculated gradient is displayed. Accordingly, the displacement or the gradient with respect to a desired direction can be known. A direction in which a point is displaced greatly can easily be found by specifying different directions. Basically, the operation for calculating the displacement or the gradient is one-dimensional operation, the operation quantity of the operation is relatively small.

The ultrasonic diagnostic apparatus in the fifth embodiment may determine the displacement or the like on the basis of the data signals directly stored in the memory 8 without being detected by the detector 5 or may determine the displacement or the like on the basis of the picture signals processed by the scan converter 6 as indicated by broken lines in FIG. 8 instead of determining the displacement or the like on the basis of the data signals detected by the detector 5. When the displacement or the like is determined on the basis of the data signals processed by the scan converter 6, the data signals before interpolation (points indicated by blank circles in FIG. 11(a)) are arranged at the corners of a square to facilitate interpolation. If the data signals are processed for sufficiently fine coordinate transformation and interpolation by the scan converter 6, the value of F (data indicated by a solid circle) may be determined as the values of the surrounding points without performing additional interpolation.

What is claimed is:

1. An ultrasonic diagnostic apparatus which receives ultrasonic waves, transmitted into a human body along a scanning line and reflected by internal organs of the human body, for producing data signals corresponding to the received, reflected ultrasonic waves, processing the data signals to generate display data, and displaying a tomogram of the human body represented by the display data, said ultrasonic diagnostic apparatus comprising:

calculating means for calculating one of a minute displacement of tissue within the human body on the basis of the data signals and a differential of the minute displacement with respect to a direction parallel to the scanning line within the human body;

local maximum calculating means, coupled to said calculating means, for calculating a plurality of temporal local maximums of one of the minute displacement varying with time and the differential of the minute displacement varying with time, and for assigning corresponding pixel data, representing levels of luminance, to each of the temporal local maximums; and display means, coupled to said local maximum calculating means, for displaying the temporal local maximums by displaying the corresponding pixel data representing levels of luminances.

2. An ultrasonic diagnostic apparatus which receives ultrasonic waves, transmitted into a human body along a scanning line and reflected by internal organs of the human body, for producing data signals corresponding to the received, reflected ultrasonic waves, processing the data signals to generate display data, and displaying a tomogram of the human body represented by the display data, said ultrasonic diagnostic apparatus comprising:

calculating means for calculating one of a minute displacement of tissue within the human body on the data signals and a differential of the minute displacement with respect to a direction parallel to a scanning line within the human body;

time calculating means, coupled to the calculating means, for calculating times corresponding to a plurality of temporal local maximums of one of the minute displacement varying with time and the differential of the minute displacement varying with time, each of said temporal local maximums having corresponding pixel data representing levels of luminances; and display means, coupled to the time calculating means, for displaying the time corresponding to the temporal local maximums by displaying the corresponding pixel data representing levels of luminances.

3. An ultrasonic diagnostic apparatus which receives ultrasonic waves, transmitted into a human body along a scanning line and reflected by internal organs of the human body, for producing data signals corresponding to the received, reflected ultrasonic waves, processing the data signals to generate display data, and displaying a tomogram of the human body represented by the display data, said ultrasonic diagnostic apparatus comprising:

calculating means for calculating one of a minute displacement of tissue within the human body and a differential of the minute displacement with respect to a direction parallel to a scanning line within the human body;

gradient calculating means, coupled to the calculating means, for calculating a gradient of a time corresponding to a temporal local maximum in one of the minute displacement varying with time and the differential of the minute displacement varying with time; and display means, coupled to the gradient calculating means, for displaying the gradient.

4. An ultrasonic diagnostic apparatus which receives ultrasonic waves, transmitted into a human body along a scanning line and reflected by internal organs of the human body, for producing data signals corresponding to the received, reflected ultrasonic waves, processing the data signals to generate display data, and displaying a tomogram of the human body represented by the display data, said ultrasonic diagnostic apparatus comprising:

calculating means for calculating one of a minute displacement of tissue within the human body and a differential of the minute displacement in a direction parallel to a scanning line within the human body;

gradient magnitude calculating means, coupled to the calculating means, for calculating a magnitude of a gradient of a time corresponding to a temporal local maximum in one of the minute displacement varying with time and the differential of the minute displacement varying with time; and display means, coupled to the gradient calculating means, for displaying the magnitude of the gradient.

5. An ultrasonic diagnostic apparatus which receives ultrasonic waves, transmitted into a human body along a scanning line and reflected by internal organs of the human body, for producing data signals corresponding to the received, reflected ultrasonic waves, processing the data signals to generate display data, and displaying a tomogram of the human body represented by the display data, said ultrasonic diagnostic apparatus comprising:

calculating means for calculating one of a minute displacement and a differential of the minute displacement with respect to a direction parallel to the scanning line within the human body;

local maximum calculating means, coupled to said calculating means, for calculating a plurality of temporal local maximums of one of the minute displacement varying with time and the differential of the minute displacement varying with time, and for assigning corresponding pixel data, having proportional luminances, to each of the temporal local maximums;

time calculating means, coupled to the calculating means, for calculating times corresponding to a plurality of temporal local maximums of one of the minute displacement varying with time and the differential of the minute displacement varying with time, each of said temporal local maximums having corresponding pixel data representing levels of luminances; and display means, coupled to the local maximum calculating means and to the time calculating means, for displaying the temporal local maximums and the time by displaying the corresponding pixel data representing levels of luminances.

6. The ultrasonic diagnostic apparatus as claimed in claim 5, further comprising gradient calculating means, coupled to the calculating means and to the display means, for calculating a gradient of the time corresponding to the temporal local maximum in one of the minute displacement varying with time and the differential varying with time, and wherein the display means further displays the gradient.

7. The ultrasonic diagnostic apparatus as claimed in claim 5, further comprising gradient magnitude calculating means, coupled to the calculating means and to the display means, for calculating a magnitude of a gradient of the time corresponding to the temporal local maximum in one of the minute displacement varying with time and the differential varying with time, and wherein the display means further displays the magnitude of the gradient.

8. An ultrasonic diagnostic apparatus which receives ultrasonic waves, transmitted into a human body along a scanning line and reflected by internal organs of the human body, for producing data signals corresponding to the received, reflected ultrasonic waves, processing the data signals to generate display data, and displaying a tomogram of the human body represented by the display data, said ultrasonic diagnostic apparatus comprising:

specifying means for specifying at least one desired point and at least one desired direction in the tomogram displayed;

calculating data generating means for generating calculating data along a line segment passing the specified desired point and extending in the specified desired direction for a plurality of tomograms produced at different times, respectively;

calculating means for calculating information on the basis of one of a displacement of the specified desired point in the specified desired direction and a rate of change of the displacement in the specified desired direction on the basis of the calculating data; and display means for displaying the information.

9. An ultrasonic diagnostic apparatus according to claim 8, wherein said information calculated by said calculating means is one of the displacement and the rate of change of the displacement.

10. An ultrasonic diagnostic apparatus according to claim 8, wherein said calculating means calculates at least one of a temporal local maximum in one of the displacement and the rate of change of the displacement, a time corresponding to the temporal local maximum, a gradient of the time and a magnitude of the gradient as said information.

11. An ultrasonic diagnostic apparatus according to claim 8, wherein said specifying means specifies a plurality of directions.

12. An ultrasonic diagnostic apparatus according to claim 8, wherein said specifying means selects at least one direction among a plurality of predetermined directions.

13. An ultrasonic diagnostic apparatus according to claim 8, wherein said specifying means specifies a plurality of points lined on a line extending in the specified direction.

14. An ultrasonic diagnostic apparatus according to claim 8, wherein said specifying means specifies a plurality of two-dimensionally arranged points.

15. An ultrasonic diagnostic apparatus which receives ultrasonic waves, transmitted into a human body along a scanning line and reflected by internal organs of the human body, for producing data signals corresponding to the received, reflected ultrasonic waves, processing the data signals to generate display data, and displaying a tomogram of the human body represented by the display data, said ultrasonic diagnostic apparatus comprising:
   calculating means for calculating one of a minute displacement and a differential of the minute displacement with respect to a direction parallel to the scanning line within the human body;
   local maximum calculating means, coupled to the calculating means, for calculating a temporal local maximum in one of the minute displacement varying with time and the differential of the minute displacement varying with time;
   gradient calculating means, coupled to the local maximum calculating means, for calculating a gradient of a time corresponding to the temporal local maximum in one of the minute displacement varying with time and the differential of the minute displacement varying with time; and
   display means, coupled to the local maximum calculating means and to the gradient calculating means, for displaying temporal local maximum, and the gradient.

16. The ultrasonic diagnostic apparatus as claimed in claim 15, further comprising gradient magnitude calculating means, coupled to the gradient calculating means and to the display means, for calculating a magnitude of the gradient of the time corresponding to the temporal local maximum in one of the minute displacement varying with time and the differential varying with time, and wherein the display means further displays the magnitude of the gradient.

17. The ultrasonic diagnostic apparatus as claimed in claim 15, further comprising gradient magnitude calculating means, coupled to the gradient calculating means and to the display means, for calculating a magnitude of the gradient of the time corresponding to the temporal local maximum in one of the minute displacement varying with time and the differential varying with time, and wherein the display means further displays the magnitude of the gradient.

18. An ultrasonic diagnostic apparatus which receives ultrasonic waves, transmitted into a human body along a scanning line and reflected by internal organs of the human body, for producing data signals corresponding to the received, reflected ultrasonic waves, processing the data signals to generate display data, and displaying a tomogram of the human body represented by the display data, said ultrasonic diagnostic apparatus comprising:
   calculating means for calculating one of a minute displacement and a differential of the minute displacement with respect to a direction parallel to the scanning line within the human body;
   gradient magnitude calculating means, coupled to the calculating means, for calculating a magnitude of a gradient of a time corresponding to a temporal local maximum in one of the minute displacement varying with time and the differential of the minute displacement varying with time; and
   display means, coupled to the gradient magnitude calculating means, for displaying the magnitude of the gradient.

19. An ultrasonic diagnostic apparatus which receives ultrasonic waves, transmitted into a human body along a scanning line and reflected by internal organs of the human body, for producing data signals corresponding to the received, reflected ultrasonic waves, processing the data signals to generate display data, and displaying a tomogram of the human body represented by the display data, said ultrasonic diagnostic apparatus comprising:
   calculating means for calculating one of a minute displacement and a differential of the minute displacement with respect to a direction parallel to the scanning line within the human body;
   time calculating means, coupled to the local maximum calculating means, for calculating a time corresponding to a temporal local maximum of one of the minute displacement varying with time and the differential of the minute displacement varying with time;
   gradient calculating means, coupled to the calculating means, for calculating a gradient of the time corresponding to the temporal local maximum in one of the minute displacement varying with time and the differential varying with time; and
   display means, coupled to the time calculating means and the gradient calculating means, for displaying the gradient and the time.

20. The ultrasonic diagnostic apparatus as claimed in claim 19, further comprising gradient magnitude calculating means, coupled to the gradient calculating means and to the display means, for calculating a magnitude of the gradient of the time corresponding to the temporal local maximum in one of the minute displacement varying with time and the differential varying with time, and wherein the display means further displays the magnitude of the gradient.

21. An ultrasonic diagnostic apparatus which receives ultrasonic waves, transmitted into a human body along a scanning line and reflected by internal organs of the human body, for producing data signals corresponding to the received, reflected ultrasonic waves, processing the data signals to generate display data, and displaying a tomogram of the human body represented by the display data, said ultrasonic diagnostic apparatus comprising:

calculating means for calculating one of a minute displacement and a differential of the minute displacement with respect to a direction parallel to the scanning line within the human body;

time calculating means, coupled to the local maximum calculating means, for calculating a time corresponding to a temporal local maximum of one of the minute displacement varying with time and the differential varying with time;

gradient magnitude calculating means, coupled to the time calculating means, for calculating a magnitude of a gradient of the time corresponding to the temporal local maximum in one of the minute displacement varying with time and the differential varying with time; and display means, coupled to the time calculating means and to the gradient magnitude calculating means, for displaying the time and the magnitude of the gradient.

22. An ultrasonic diagnostic apparatus which receives ultrasonic waves, transmitted into a human body along a scanning line and reflected by internal organs of the human body, for producing data signals corresponding to the received, reflected ultrasonic waves, processing the data signals to generate display data, and displaying a tomogram of the human body represented by the display data, said ultrasonic diagnostic apparatus comprising:

calculating means for calculating one of a minute displacement and a differential of the minute displacement with respect to a direction parallel to the scanning line within the human body;

gradient calculating means for calculating a gradient of a time corresponding to a temporal local maximum in one of the minute displacement varying with time and the differential varying with time, and a gradient magnitude calculating means, coupled to the gradient calculating means, for calculating a magnitude of the gradient of the time corresponding to the temporal local maximum in one of the minute displacement varying with time and the differential varying with time; and display means, coupled to the gradient calculating means and to the gradient magnitude calculating means, for displaying the gradient and the magnitude of the gradient.

* * * * *

UNITED STATES PATENT AND TRADEMARK OFFICE
CERTIFICATE OF CORRECTION

PATENT NO. : 5,355,887
DATED : October 18, 1994
INVENTOR(S) : Miyuki IIZUKA et al.

It is certified that error appears in the above-indentified patent and that said Letters Patent is hereby corrected as shown below:

Column 1, line 8, change "by" to --by,--;

line 22, change "organs" to --organs,--;

line 26, after "and" insert --displays--;

line 33, change "PP." to --pp.--; and line 35, before "reference" delete "the".

Column 2, line 29, change "finding" to --finding,--.

Column 3, line 60, change "is" to --are--.

Column 4, line 16, before "and" insert --...--;

line 56, in front equation insert --|--.

Column 6, line 12, change "tomogram" to --tomograms--;

line 32, change "may specify" to --specifies--;

line 42, change "lives" to --liver--;

line 44, change "lives" to --liver--; and line 67, change "calculates" to --calculate--.

UNITED STATES PATENT AND TRADEMARK OFFICE
CERTIFICATE OF CORRECTION

PATENT NO. : 5,355,887
DATED : October 18, 1994
INVENTOR(S) : Miyuki IIZUKA et al.

It is certified that error appears in the above-indentified patent and that said Letters Patent is hereby corrected as shown below:

Column 11, line 6, change "unit" to --units--;

line 34, change "is" to --are--; and line 36, delete "unit" (first occurrence).

Columm 12, line 7, change "of" to --or--; and line 12, change "of" to --or--.

Signed and Sealed this

Fourteenth Day of March, 1995

Attest:

BRUCE LEHMAN

*Attesting Officer*　　　*Commissioner of Patents and Trademarks*